United States Patent [19]

Harrell et al.

[11] Patent Number: 5,132,084
[45] Date of Patent: Jul. 21, 1992

[54] APPARATUS AND METHODS FOR DISPENSING WATER TO A STERILIZING CHAMBER OF AN AUTOCLAVE

[75] Inventors: Duronnie L. Harrell; Ye Mu, both of Charlotte, N.C.

[73] Assignee: The Pelton & Crane Company, Charlotte, N.C.

[21] Appl. No.: 590,270

[22] Filed: Sep. 28, 1990

[51] Int. Cl.⁵ .............................. A61L 2/06; G05D 7/00
[52] U.S. Cl. ........................................ 422/26; 422/110; 422/115; 422/116; 422/119; 422/295; 422/299
[58] Field of Search ................ 422/26, 106, 110, 113, 422/115, 116, 119, 295, 298, 299

[56] References Cited

U.S. PATENT DOCUMENTS

| | | | |
|---|---|---|---|
| 3,571,563 | 3/1971 | Shulz | 422/119 |
| 4,108,601 | 8/1978 | Wolft | 422/295 |
| 4,397,814 | 8/1983 | Darecchio | 422/298 |
| 4,447,399 | 5/1984 | Runnels et al. | 422/113 |
| 4,808,377 | 2/1989 | Chiders et al. | 422/26 |
| 4,865,814 | 9/1989 | Childress | 422/26 |
| 4,891,188 | 1/1990 | Albright et al. | 422/26 |

*Primary Examiner*—Robert J. Warden
*Assistant Examiner*—Theresa A. Trembley
*Attorney, Agent, or Firm*—Lawrence C. Edelman

[57] ABSTRACT

There is disclosed an autoclave system incorporating a sterilization chamber and a reservoir. The reservoir is coupled to the sterilization chamber by means of a selectively operated valve. A microcontroller in conjunction with timing means computes a time necessary to place a predetermined amount of water into the sterilization chamber to assure that a proper sterilization cycle will be implemented. The apparatus determines the amount of time required to operate the valve based on the water level in the reservoir. The system is initilized with a full reservoir of water and bases all successive computations for valve operation from this point. Thus the valve is operated according to a given time duration, which time duration is computed according to the number of sterilization cycles previously performed by the autoclave system.

19 Claims, 1 Drawing Sheet

APPARATUS AND METHODS FOR DISPENSING WATER TO A STERILIZING CHAMBER OF AN AUTOCLAVE

FIELD OF THE INVENTION

This invention relates to apparatus and a method for determining an amount of water to be let out of a reservoir and into a sterilizer for subsequent heating of the water into a sterilizing steam and more particularly to a method and apparatus employing controlled timing of a valve to dispense a predetermined amount of water to a sterilizing chamber of an autoclave.

DESCRIPTION OF THE PRIOR ART

The prior art arrangements for sterilizing apparatus typically include a liquid reservoir or supply tank, a dose tank and a three-way valve for controlling the flow of liquid from the supply tank into the dose tank and from there into the heating chamber of the sterilizer. The purpose of the dose tank is to supply a precisely predetermined dose or pre-measured amount of liquid (such as water) into the sterilizer chamber of the autoclave. In this manner the proper amount of steam can be generated from the water for sterilizing items which have been positioned or placed inside the chamber. German patents 3,025,928 and 3,409,365 are typical of such arrangements and require three connecting tubes or lines, each line having a fitting at each of its ends, for connecting together the supply tank, the dose tank, the chamber and the three-way valve. U.S. Pat. No. 4,865,814 entitled Automatic Sterilizer issued on Sept. 12, 1989 to B. B. Childress and assigned to the assignee herein shows a microprocessor controlled sterilizer employing a dose tank and associated apparatus. Thus as one can ascertain, the prior art techniques utilize a dose tank to assure that a given pre-determined amount of water is always supplied to the sterilization chamber in order to produce the optimum amount of steam necessary for operation of the autoclave. Thus as the prior art was cognizant of, the steam sterilization system including the sterilizing chamber required a pre-determined amount of water which was supplied by the dose tank. U.S. Pat. No. 4,447,399 entitled Combination Steam and Unsaturated Chemical Vapor Sterilizer issued on May 8, 1984 to R. R. Runnells et al describes another prior art autoclave. In order to accomplish sterilization and control, the patent describes a special three-way valve for dispersing measured quantities of liquids. The three-way valve includes a suitable vessel or compartment therein enabling the valve to dispense pre-determined quantities of water or chemicals. It is noted that the use of dose tanks is generally undesirable due to their requirement of extra fluid connections which can become unreliable and leak.

Additionally, prior art systems employ gravity feed of water into the chamber. In these systems water from a reservoir is fed into the chamber by the force of gravity. This presents no problem as long as the sterilization chamber is cold or at a temperature below the boiling point of water. However, if the chamber is hot (e.g., above the boiling point of water) there is a premature pressure build-up in the chamber, even though the chamber is not being heated, which will prevent the gravity feed of water into the chamber. This situation can occur when two successive sterilization cycles are run back to back with no substantial cool-down time between cycles. Thus, the chamber is filled with an insufficient amount of water to operate in a complete sterilization cycle. Furthermore, if the chamber is hot enough, then no water is allowed to enter the chamber. It would be desirable to prevent improper filling due to premature pressure build-up.

To circumvent these problems, in accordance with one aspect of the present invention, the amount of water directed to the chamber is under control of a filling procedure based upon the water level in an external reservoir.

In accordance with the present invention, one also completely eliminates the dosing chamber by controlling the amount of water which is dispensed to the sterilization chamber by means of a timed operation of a fill valve. In this manner the fill valve, which is connected directly to the reservoir, is controlled according to pre-determined time intervals to automatically enable the correct amount of water to be dispensed into the sterilization chamber during system operation. As one can ascertain, the present invention is extremely desirable in that it minimizes the complexity of the system by eliminating various parts thereof, thereby improving system reliability and cost effectiveness.

SUMMARY OF THE INVENTION

The amount of water required to be directed to a sterilization chamber is determined by the calculation of a timing interval and is derived based on the water level in an external reservoir. The system is initialized with a full reservoir of water and bases all successive calculations for fill timing from this level. In addition to the external water reservoir, the system includes two suitably sized orifices or ports controlled by two solenoid valves. One valve is a fill valve which is timed in operation to allow water into the chamber and the other valve is a vent valve for venting premature exhaust pressure. A micro-controller controls the timing for the fill solenoid, detects the temperature and pressure levels inside the chamber and controls the venting solenoid as well as the general operation of the sterilizer.

BRIEF DESCRIPTION OF THE DRAWINGS

The sole figure, in block form, depicts the basic electronic and mechanical portions of a sterilizer or autoclave constructed in accordance with the principles of the present invention.

DETAILED DESCRIPTION OF THE PREFERRED EMBODIMENT

Figure 1:
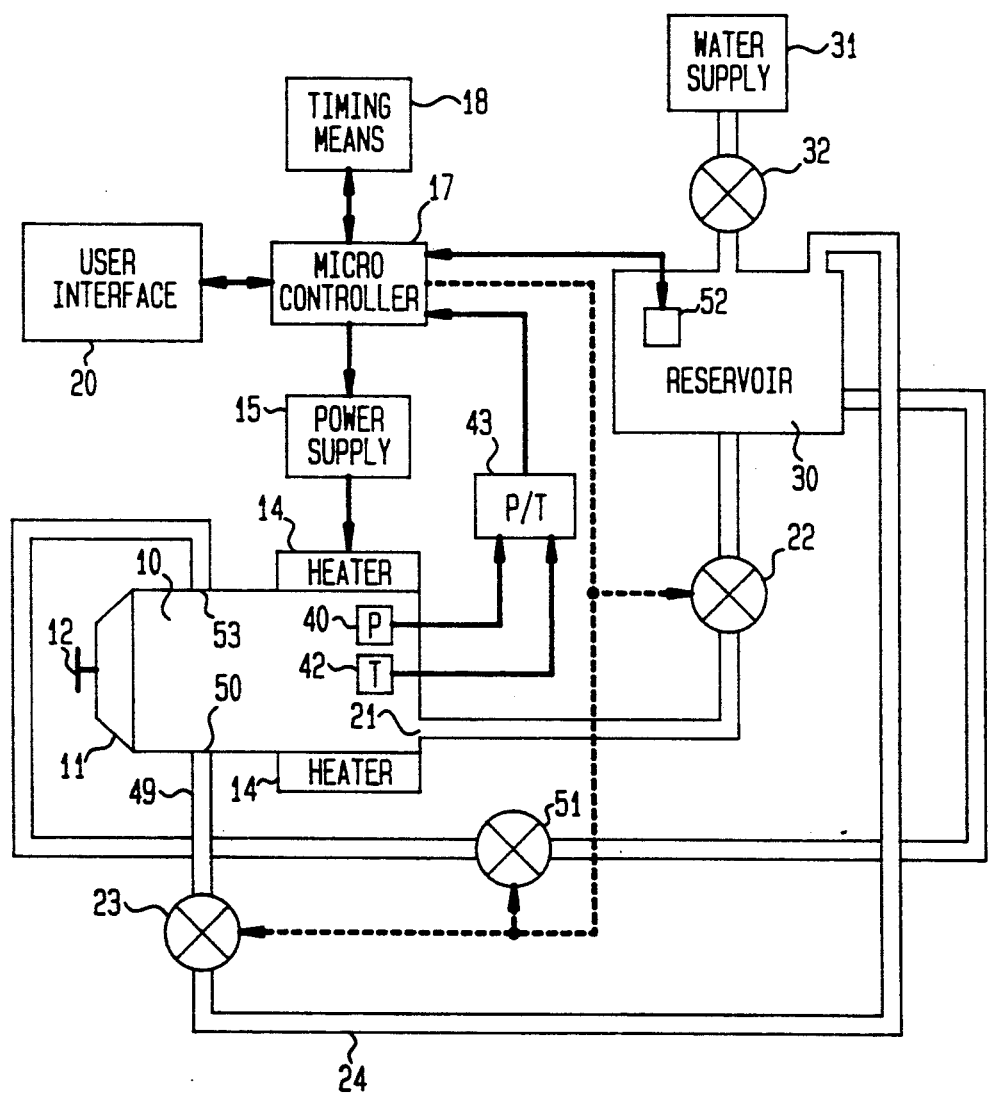

There is shown a sterilizing chamber 10 having a door 11 operated by a handle 12 for allowing access by a user to the interior of the chamber 10 for placing items to be sterilized therein. As can be seen, the chamber is associated with a heater 14 which heater is supplied power by means of a power supply 15 under the control of a microcontroller or microprocessor module 17. As will be explained, the microprocessor module 17 further includes or is associated with timing means 18. Timing means 18 operates in a manner to determine and control the amount of water to be directed to the pressure chamber 10 by providing selected operating time durations to a fill valve 22. The microcontroller is associated with a user interface 20. The user interface 20 may consist of a typical display panel together with a series of operating controls and switches to enable the user to set the particular mode of operation for the sterilization or pressure chamber 10. Pressure chamber 10 contains an input port 21 which receives water via a fill valve 22.

The fill valve 22 is operated in a novel manner, as will be explained, by the timing means 18 and microcontroller 17 and, for example, may be an electrically operated valve such as a solenoid valve. The input port of fill valve 22 is coupled to an output port of a reservoir 30. The reservoir 30 contains a given amount of water which is supplied by means of a typical water supply 31 through a valve 32. The valve 32 may be manually or automatically operated as is well known. The reservoir feeds water into the chamber 10 by means of gravity and only when the fill valve 22 is opened. The sterilization chamber 10 is also associated with an output port or vent orifice 50 which is coupled to a vent valve 23 via a passageway 49. The output of the valve 23 is coupled to a suitable venting passageway 24 which is directed back into the reservoir 30. During the sterilization cycle, the vent valve 23 and the fill valve 22 are closed. However, while steam is initially being generated inside the chamber 10, vent orifice 50 periodically vents the air which is being displaced from the chamber by the steam, as well as cool steam, into the reservoir 30 via passageway 49. This is known as preconditioning, which occurs before the sterilization cycle is begun. Also shown is a dump valve 51 which is also operated by microcontroller 17. The dump valve 51 is coupled to a top orifice 53 associated with the sterilization chamber 10 which is larger than vent orifice 50. The dump valve opens only at low pressures to speed up the release of pressure from the chamber 10 at the end of the sterilization cycle and during the fill cycle. The output port of the dump valve also returns to the reservoir. The vent valve 23 has the output conduit 24 coupled via a coil to condense steam from the vent to water in the reservoir. Typically associated with the chamber 10 is a pressure sensor 40 and a temperature sensor 42. Both the pressure and temperature sensors are directed to a suitable processing module 43 for converting, for example, the analog outputs of the sensors into digital signals which are directed to and stored in the microcontroller for utilization by the microcontroller and for further processing.

In operation, the user selects an operating mode for the sterilizer as, for example, a preset time/temperature/pressure cycle for sterilizing different types and quantities of items which are placed inside the sterilization chamber 10. These items, for example, can constitute wrapped or unwrapped instruments. The user selects the various operating parameters as described above by means of the user interface 20 which, for example, as indicated, may utilize control switches and other suitable control mechanisms. This information is directed to the microcontroller or microprocessor 17 which supplies proper operating signals in order to implement the operation as specified by the user interface. Although any conventional operation can be used for sterilization and drying, in the preferred embodiment, the operation of the sterilization and drying cycles of the sterilizer are as described in U.S. Pat. No. 4,865,814 entitled Automatic Sterilizer and issued Sep. 12, 1989 to Bobby B. Childress and assigned to the same assignee as the present invention, and which is incorporated herein by reference.

According to prior art techniques, a dosing chamber which was coupled to the reservoir 30 insured that precise amounts of water would enter the sterilization chamber 10 so that enough steam could be generated to properly sterilize the items that were placed inside the chamber. For example, if an insufficient amount of water were placed in the chamber, steam would not be generated throughout the full duration of the sterilizing cycle and therefore improper sterilization would occur. On the other hand, if too much water were introduced into the pressure chamber the operation would take an excessive amount of time to produce the required amount of steam also resulting in improper operation and inefficient sterilization.

In the present embodiment, a level switch 52 is present in reservoir 30. When the reservoir 30 is filled, switch 52 closes. Switch 52 is coupled to the microprocessor 17 so that the fill condition of the reservoir 30 is known. In the present invention microcontroller 17 is responsive to control signals from the user interface 20 for controlling a timed operation of the fill valve 22, operation of vent valve 23 and the dump valve 51, as well as the power supply 15 which in turn operates the heater 14. In this manner the microcontroller 17 determines the amount of water which will enter the sterilization chamber, in contrast to the prior art technique of a dose tank, as well as controlling the power supply 15 which supplies power to the heater 14 to generate sterilizing steam inside chamber 10 during a sterilizing cycle and to further control the heat inside the chamber during a drying cycle. The microcontroller 17 also provides signals to the user interface 20 in order to present information to the user concerning the status and operation of the sterilizer. The pressure and temperature module 43, which as indicated is coupled to the pressure sensor 40 and temperature sensor 42, monitors the pressure and temperature inside the chamber 10 for utilization by microcontroller 17 for controlling the steam generation during the sterilizing cycle and furthermore the temperature during the drying cycle. Except for certain details to be explained regarding the operation of the fill valve by means of the microcontroller, the operation of the sterilizing apparatus as particularly described above is of conventional design and operates in a conventional manner.

As briefly indicated above, the major difference between the apparatus depicted in the figure and prior art units is the novel timed operation of the fill valve 22 as controlled directly from the microcontroller 17. In this manner, the apparatus depicted in the figure completely eliminates the dosage tank necessary for prior art operation. The particular operation of the autoclave depicted in the figure will now be explained.

Initially, the reservoir 30 is filled to capacity. This condition is recognized by the microcontroller 17 via the operation of the level switch 52 indicating a full reservoir. Therefore, there exists a known head pressure in the reservoir. At this point in time the microcontroller including the timing means 18 calculates the required amount of time to allow a pre-determined amount of water into the chamber suitable for a sterilization cycle. This time is normally the minimum time required, based on a cold chamber. Initially as one can understand, the chamber is cold and there is, therefore, no back pressure from steam which can build-up when, for example, cold water enters a hot chamber. With each successive filling operation, the calculated fill time is lengthened to account for a reduced head pressure, because only a certain percentage of the water which was directed through the fill valve 22 into the chamber during the prior operation is extracted out of the chamber and back into the reservoir 30. This can occur by means of the vent and dump outputs of the chamber which, as indicated, are directed back into the reservoir 30. This percentage is known and, for example, about 10% of the water is lost in each sterilization cycle. Since the system is closed, this loss of water is mainly due to evaporation. This percentage is used in the fill time calculation and also serves as an indicator to the controller when the reservoir has insufficient water to complete another cycle. When the controller senses a given number of cycles have occurred and determines that the reservoir is too low in water, the operator is then given an indication to refill the reservoir 30. This indication is a visual or audible signal located or directed to the user interface 20. Refilling of the reservoir 30 is accomplished by accessing the water supply 31 via a suitable valve or control member 32.

The process of directing water into chamber 10 and extracting water from the chamber is as follows. The controller 17 first opens both fill and vent solenoid valves 22 and 23 in an attempt to allow water into the chamber 10. The controller 17 monitors the pressure inside the chamber 10 by means of the pressure sensor 40. If the pressure inside the chamber is not atmospheric (i.e., there is a pressure build-up due to water entering a hot chamber) then the controller 17 causes fill valve 22 to close and the vent valve 23 remains opened to reduce the pressure. The fill valve 22 is closed during these conditions to prevent water inside the chamber 10 from backing up into the reservoir 30. Furthermore, the timing means 18 during this condition is stopped. In a similar manner, if the pressure in the chamber 10 is atmospheric, then the fill valve 22 is opened for a predetermined time interval calculated to result in the proper amount of water to flow into chamber 10 from reservoir 30. In the preferred embodiment, the fill time interval is broken-up into ten-second intervals wherein for nine seconds valve 22 is opened and then closed for one second. During each fill time interval this valve pulsing sequence is repeated, as for example 15 opened for nine seconds and closed for one second. The pulsing of the fill valve 22 by the controller prevents the tendency of the valve to stick or jam.

The time of operation for the fill valve is calculated by the microprocessor. This time is, for example, inserted in a down counter (not shown) associated with microprocessor 17. The output of the down counter, if not zero, operates the fill valve 22, keeping the valve opened. Every nine seconds the fill valve is closed for one second and then opened for nine seconds. The down counter does not decrement for the one second valve closure period, but decrements for the nine second valve open period, until the count reaches zero, thereby indicating that the computed fill time interval is over, the fill valve 22 should be closed, vent valve 23 should be opened and preconditioning for the sterilization cycle begun. The controller 17 also monitors the temperature of the chamber 10 via the sensor 42. If the temperature is greater than 101° C, the count-down timer incorporated in the timing means 18 is stopped. This is to enable the chamber to cool off. If the temperature is less than 101° C the timer is started and the fill cycle is commenced. The timer is programmed to count down from a preset fill-time wherein:

Fill time = 66 + 5x(cycle #)

cycle # = number of cycles being run after the level switch 52 is opened.

The equation is applicable for a reservoir 30 having a liquid capacity of three quarts with a fill orifice of 3/16 of an inch in diameter. The equation for fill-time is based on experimentation and such equations can be implemented for other capacity reservoirs.

Thus, with a cold chamber, the fill valve is left opened for the required amount of time to fill the chamber with a pre-determined amount of water. With a hot chamber, if premature pressure is detected the timing process is stopped and the fill valve is closed until the premature pressure is depleted through the still opened vent valve. At this time, the fill valve is re-opened and the timer restarted. This process is repeated until the timer has exhausted its count. With each attempt to fill the chamber, the chamber 10 is cooled. This is due to the transfer of water to the chamber from the reservoir. After filling the sterilization chamber, the sterilization process is started. Thus, once the proper amount of water is located inside the sterilization chamber, the microcontroller monitors the pressure and temperature conditions inside chamber 10 while activating the power supply 15 which in turn operates the heater 14 for carrying-out a conventional type of sterilization and drying cycles, such as described in the forenoted U.S. Pat. No. 4,865,814. In the preferred embodiment, a pre-conditioning cycle is also used before the start of sterilization to vent air from chamber 10 using vent orifice 50 and valve 23 in a manner such as described in U.S. Pat. No. 3,494,725 issued on Feb. 10, 1970 to A. S. Irons et al. and entitled Pulsing Process of Sterilization.

After a pre-determined pressure/temperature has been maintained for a pre-determined amount of time as determined by the microcontroller 17, the sterilize cycle is over and the microcontroller 17 causes the vent valve 23 to open. During this time the steam pressure inside the chamber decreases and the steam condenses whereby any residual water can be returned to the reservoir via the conduit 24. Thus after sterilization, the chamber 10 will have a large volume of pressurized steam which is used for extracting the water. After a cycle is complete, the vent valve 23 is opened for a time period as required to release all the pressure except for amounts sufficient to push the water out of the chamber. In this manner, the pressure goes from 225 KPA to 40 KPA. At 40 KPA the vent valve 23 is closed and the fill valve 22 is opened and water is extracted from the chamber because the fill valve is under the water line. The pressure in the chamber remains relatively constant until all the water has been extracted and then the pressure will continue to fall rapidly. At 20 kPa the fill valve 22 is closed and the vent and dump valves 23 and 51 are opened to quickly release the remaining pressure to atmospheric. Now the cycle can be repeated, only this time new values are calculated for the fill time. These values, for example, are determined and based upon how many fill or sterilization cycles were implemented before and according to the fill-time equation for the reservoir. After each fill cycle there is less water pressure in the reservoir and therefore it takes longer to drain out the required amount of water. Thus, the above apparatus relies upon control of both the fill and the vent valves by means of timing means where given time durations are generated by the microprocessor in accordance with the previous number of cycles implemented by the system. The above apparatus implements time control of the fill valve and the vent valve to determine the amount of water to be let into and out of the sterilizing chamber and the reservoir for providing efficient operation without the necessity of incorporating a dosage chamber.

Thus, there has been shown and described a novel method and apparatus for dispensing water into a sterilizing chamber which fulfills all the objects and advantages sought therefore. Many changes, modifications, variations and other uses and applications of the subject invention will, however, become apparent to those skilled in the art after considering this specification and the accompanying drawings which disclose a preferred embodiment thereof. All such changes, modifications, variations and other uses and applications which do not depart from the spirit and scope of the invention are deemed to be covered by the invention which is limited only by the claims which follow.

We claim:

1. In a sterilizing apparatus of the type employing a sterilization chamber for receiving items to be sterilized, said sterilization chamber coupled to a reservoir via a selectively activated valve to enable water to enter said sterilization chamber via said selectively valve when said selectively activated valve is activated and including means coupled to said sterilization chamber for converting said water into steam at a given monitored temperature and pressure to sterilize said items during a sterilization cycle, the combination therewith of apparatus for controlling said selectively activated valve the improvement, comprising:

timing means coupled to a selectively activated valve and adapted to activate the same until a given time duration is depleted, said given time duration determined according to the amount of water necessary to implement the next sterilization cycle, whereby said time duration is calculated according to the number of sterilization cycles previously implemented; and processing means responsive to a pressure monitored within said sterilization chamber, wherein when the monitored pressure exceeds a predetermined level said processing means delays activation of said selectively activated valve and suspends depletion of said determined time duration while said activation is delayed.

2. The apparatus according to claim 1, wherein said given time duration is calculated according to the following equation:

$$T = 66 + 5 \times (Cycle \#)$$

T = Time Duration
Cycle # = Number of sterilization cycles run after a full reservoir.

3. The apparatus of claim 1, wherein said timing means includes:

an auxiliary timing means for causing said selectively activated valve to be activated in a pulse manner during said time duration.

4. A method for filling a sterilization chamber with water held in a reservoir, comprising the steps of:

providing a sterilization chamber with water held in a reservoir;
determining the level of water in said reservoir;
providing a flow path for selectively allowing water to enter said sterilization chamber from said reservoir;
computing a time duration which will allow water from said reservoir to enter said sterilization chamber via said flow path, said time duration being computed according to the number of sterilization cycles previously performed;
selectively controlling said flow path to allow flow to said sterilization chamber for said computed time duration; and
monitoring the pressure inside said sterilization chamber to determine if the pressure is above a given value which will not allow water to freely enter said sterilization chamber, whereby when said monitored pressure is above said given value, said flow path is further controlled so that water is not allowed to flow to said sterilization chamber.

5. The method according to claim 4, further including the step of:

monitoring both the pressure and temperature in said sterilization chamber to determine if they are within a predetermined desirable pressure and temperature range which would allow water to freely enter said sterilization chamber for said computed time duration if said monitored temperature and pressure are within said predetermined desirable range and when either one of said pressure and temperature inside said sterilization chamber exceeds said desireable range, said flow path is controlled so that water is not allowed to flow to said sterilization chamber.

6. The method according to claim 4, further including the step of:

venting the sterilization chamber when said monitored pressure is above said given value, to thereby reduce the pressure in said sterilization chamber.

7. The method according to claim 6, wherein the step of monitoring includes:

monitoring the temperature inside said sterilization chamber to determine whether the temperature is above the boiling point of water and if said temperature is above said boiling point said flow path is controlled so as to prevent water from entering said sterilization chamber and if said temperature is below said boiling point said flow path in controlled so as to allow water to enter said sterilization chamber.

8. The apparatus for dispensing water in an autoclave system, said system of the type capable of performing a sterilization cycle to sterilize items, comprising:

a reservoir for containing a given quantity of fluid,
means coupled to said reservoir to provide a control signal when said reservoir contains said given quantity of fluid,
selectively operated valve means coupling said reservoir to a sterilization chamber to enable fluid to flow from said reservoir to said sterilization chamber when said selectively activated valve is operated in a first mode and to prevent flow from said reservoir when said selectively activated valve is operated in a second mode,
computing means responsive to said control signal for calculating a time duration signal according to the number of sterilization cycles previously performed by said autoclave system,
means for monitoring at least one of the pressure and temperature of said sterilization chamber to provide an indication signal when said one of pressure and temperature is within a given desirable range, and
timing means coupled to said selectively activated valve means and responsive to said time duration signal and indication signal to operate said selectively activated valve in said first mode for a time according to said time duration signal.

9. The apparatus according to claim 8 further comprising:
venting means coupled to said sterilization chamber for venting said sterilization chamber when said monitored pressure is above a desirable value.

10. The apparatus according to claim 8, wherein said computing means and said timing means include a microprocessor.

11. Apparatus for dispensing water in an autoclave system, said autoclave system of the type capable of performing sterilization cycles to sterilize items, comprising:
a sterilization chamber for receiving items to be sterilized,
a reservoir for containing a given quantity of water,
means coupled to said reservoir to provide a control signal when said reservoir contains said given quantity of water,
selectively operated valve means coupling said reservoir to said sterilization chamber to enable water to flow from said reservoir to said sterilization chamber when said selectively activated valve is operated in a first mode and to prevent flow when said selectively activated valve is operated in a second mode,
means coupled to said sterilization chamber to monitor at least one of the temperature and pressure thereof to provide at least one of a temperature and pressure signal according to a corresponding temperature and pressure within said sterilization chamber,
microcontroller means responsive to said control signal and said at least one temperature and pressure signal to provide a time duration signal at an output for operating said selectively activated valve in a first mode means when said at least one of pressure and temperature is within a desirable range and for a time according to said time duration signal which is computed by said microcontroller to provide a time duration for operating said selectively activated valve in said first mode according to the number of sterilization cycles previously performed by said autoclave system.

12. The apparatus according to claim 11, further including venting means coupled to said sterilization chamber and operated by said microprocessor to vent said sterilization chamber prior to operation of said selectively activated valve means for given pressure levels.

13. The apparatus according to claim 11, further including means for operating said selectively activated valve for a predetermined ON and a predetermined OFF period over said given time duration whereby said selectively activated valve is operated at a given duty cycle.

14. The apparatus according to claim 11, further including means responsive to said time duration signal to provide an indication when said reservoir requires additional water.

15. The apparatus according to claim 11, wherein said time duration signal (T) is computed according to the following equation:

$$T = 66 + 5 \times (\text{Cycle } \#)$$

where Cycle # is the number of previously performed sterilization cycles.

16. The apparatus according to claim 11, wherein said microcontroller is responsive to said pressure signal whereby if said pressure is above a given value and said selectively activated valve means is operating in said first mode, said selectively activated valve means is caused to operate in said second mode until said pressure is within said desirable range.

17. The apparatus according to claim 11, wherein said microcontroller is responsive to said temperature signal indicative of said temperature being below the boiling point of said water to cause operation of said selectively activated valve means in said first mode and to cause operation of said selectively activated valve means in said second mode when said temperature is above said boiling point.

18. The apparatus according to claim 11, further including means responsive to a given number of performed sterilization cycles to provide an indication that said reservoir requires refilling.

19. The apparatus according to claim 11, wherein said means coupled to said reservoir is a level switch which provides a closure when said reservoir is filled.

* * * * *